United States Patent [19]
Archer et al.

[11] Patent Number: 5,745,350
[45] Date of Patent: Apr. 28, 1998

[54] POWER SUPPLY CIRCUIT WITH A WIDELY VARYING INPUT VOLTAGE

[75] Inventors: Stephen T. Archer, Sunnyvale; Kenneth J. Carroll, Los Altos, both of Calif.

[73] Assignee: Pacesetter, Inc., Sunnyvale, Calif.

[21] Appl. No.: 660,411

[22] Filed: Jun. 7, 1996

[51] Int. Cl.$^6$ ............................................. H02M 3/22
[52] U.S. Cl. ......................................... 363/15; 363/80
[58] Field of Search .................... 363/15, 20, 80, 363/97, 101, 124, 131; 607/5, 7; 320/33, 40

[56] References Cited

U.S. PATENT DOCUMENTS

| | | | |
|---|---|---|---|
| 4,384,321 | 5/1983 | Rippel | 363/124 |
| 4,437,146 | 3/1984 | Carpenter | 363/21 |
| 4,548,209 | 10/1985 | Wielders et al. | 128/419 |
| 4,584,514 | 4/1986 | Kaminski | 320/33 |
| 4,797,541 | 1/1989 | Billings et al. | 235/449 |
| 5,010,469 | 4/1991 | Bobry | 363/37 |
| 5,251,624 | 10/1993 | Bocek et al. | 607/6 |
| 5,265,588 | 11/1993 | Nelson et al. | 607/5 |
| 5,488,553 | 1/1996 | Renger | 363/21 |
| 5,554,174 | 9/1996 | Causey, III | 607/5 |

*Primary Examiner*—Adolf Berhane
*Attorney, Agent, or Firm*—Steven M. Mitchell

[57] ABSTRACT

In a power supply circuit supplying a high voltage charger of an implantable cardioverter-defibrillator (ICD), a changer circuit switches the power source of the power supply circuit between a battery and an output signal of a step-up converter. The signal derived from the boost winding rises to a high voltage when the high voltage charger charges the storage capacitors of the ICD. A system current measurement circuit can be provided in the power supply circuit.

7 Claims, 7 Drawing Sheets

POWER SUPPLY CIRCUIT WITH A WIDELY VARYING INPUT VOLTAGE

BACKGROUND OF THE INVENTION

1. Field of the Invention

The present invention relates to electronic circuits; in particular, the present invention relates to a power supply circuit which maintains steady output voltages despite a widely varying input voltage.

2. Discussion of the Related Art

Implantable cardioverter-defibrillators (ICDs) have been used in patients with cardiac tachyarrhythmias. For example, one such ICD is described in U.S. Pat. No. 5,048,521 to B. Pless et al, entitled "Method for Combined Cardiac Pacing and Defibrillation", assigned to Ventritex, Inc., and issued on Sep. 17, 1991. In such an ICD, a high voltage charger is provided to charge one or more storage capacitors to a high voltage. Upon detecting a ventricular fibrillation in the patient, these capacitors are quickly charged and then discharged through the patient's heart to deliver one or more high energy shocks for defibrillating the patient's heart.

Because high voltage charging in the ICD draws a large current from the battery, the battery voltage may dip below an acceptable level necessary for logic circuits to operate correctly. To prevent such dip in voltage, the charging current that can be drawn from the battery source must be limited, resulting in impairment of the ICD's ability to rapidly charge the storage capacitors and to deliver therapy following detection of the arrhythmia. Otherwise, a relatively more bulky battery must be selected, resulting in a larger and less acceptable device.

SUMMARY OF THE INVENTION

In accordance with the present invention, a power supply circuit in an implantable cardioverter defibrillator (ICD) includes a changer which selects, as a power source for the power supply circuit, either a battery or a signal derived from the output voltage of the boost windings in a high voltage transformer. The signal derived from the output voltage of the boost windings is selected when the ICD is charging the storage capacitors. The output signal of the changer is used to derive all power supply output signals. Among the regulated power supply output signals is a voltage reference signal which is generated using a semiconductor bandgap voltage. The switching off of a charge current during the charging of the storage capacitors results in a magnetic field which provides an output voltage in the boost windings. The output voltage can be used as an alternative power source of the power supply circuit.

In accordance with another aspect of the present invention, the power supply circuit includes a current measuring circuit for measuring the total current in the ICD, except for the high voltage charging current. Such a current measuring circuit includes a resistor of known value coupled between a battery power source and the circuits of the ICD. An amplification circuit coupled to the resistor provides an output signal. This output signal can be selectively coupled to the resistor, so that the output signal represents either (i) the current in the resistor; or (ii) a calibration current. The difference between the calibration current and the current in the resistor is proportional to the total current in the ICD.

The present invention allows the regulated output voltages of the power supply circuit to be stable, even though the battery output voltage may fall below the voltage necessary to generate these regulated output voltages.

The present invention is better understood upon consideration of the detailed description below and the accompanying drawings.

DETAILED DESCRIPTION OF THE PREFERRED EMBODIMENTS

Figure 1:
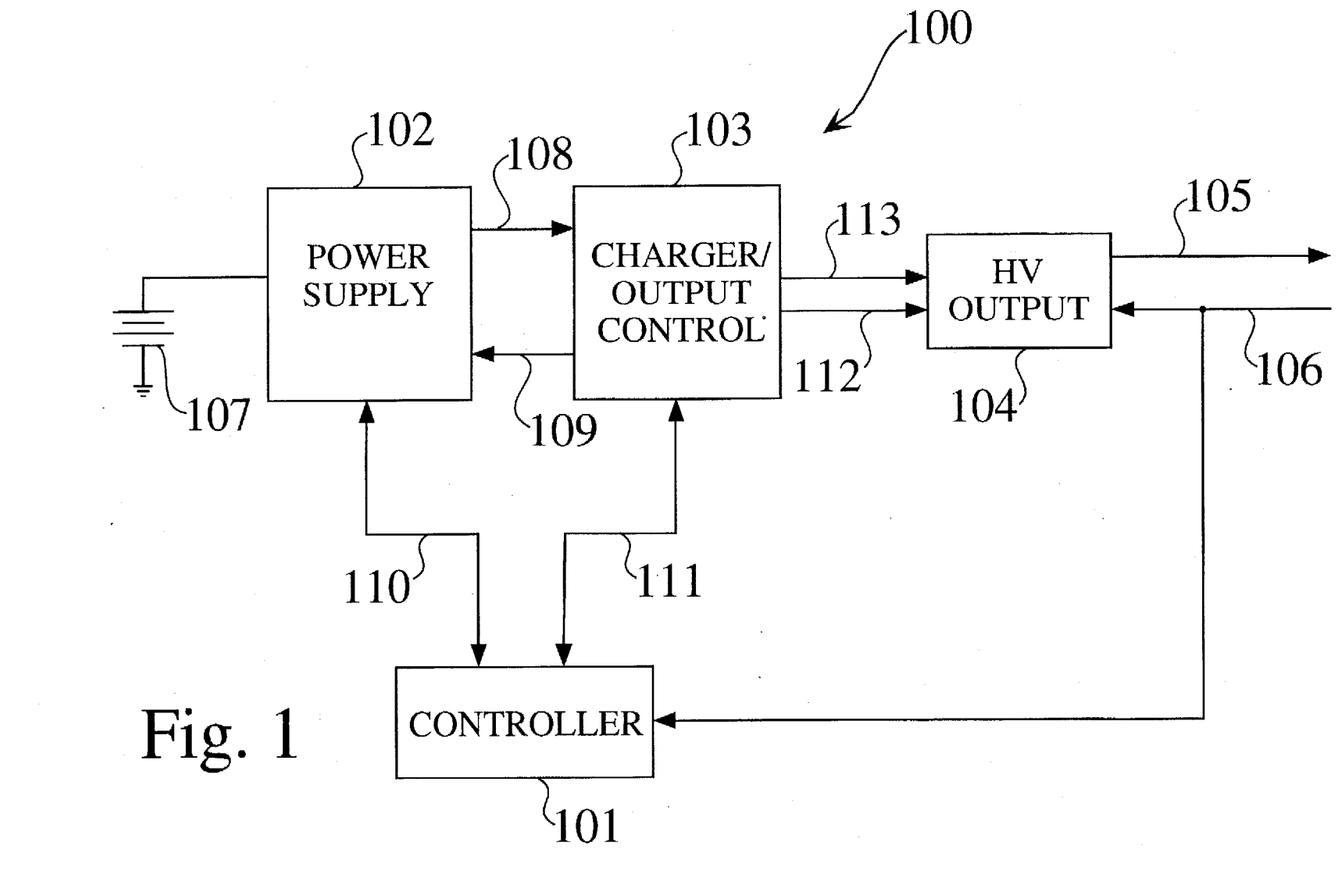
FIG. 1 is a block diagram of an ICD in which the present invention can be implemented.

The present invention can be implemented in conjunction with a high voltage charger of an implantable cardioverter-defibrillator ICD. An example of such an ICD (ICD 100) is shown in FIG. 1 in block diagram form. In FIG. 1, ICD 100 is powered by a battery 107. Battery 107 provides all the energy needs of ICD 100. Power supply circuit 102 generates the various voltage levels needed to operate ICD 100. In accordance with the present invention, power supply circuit 102 draws power from both battery 107 and a signal "VBOOST" generated by a high voltage charger/output controller circuit 103. Signal VBOOST is represented generally by terminal 109 in FIG. 1. The various voltages generated by power supply circuit 102 which are provided to high voltage charger/output controller circuit 103 are represented generally by terminal 108.

As mentioned above, high voltage charger/output controller circuit 103 generates signal VBOOST for use by power supply circuit 102. High voltage charger/output controller circuit 103 controls both the charging and the discharging of the storage capacitors in high voltage output circuit 104. Terminal 105 represent the leads coupled to the implanted defibrillation electrodes, at least one of which is placed in or near the patient's right ventricle. Terminal 106 represent leads for sensing the electrical activity in the patient's heart.

Controller 101, which includes a microprocessor and a static random access memory, controls the overall operation of the ICD 100. Controller 101 includes a waveform analyzer for detecting arrhythmias in the patient's heart from the sensed electrical signals. Controller 101 also includes various timers, and a pacing circuit for low voltage level pacing. Low voltage level pacing operation of ICD 100 is described in copending patent application METHOD AND APPARATUS FOR INDUCING FIBRILLATION, Ser. No. 08/568036, filed Dec. 6, 1995, assigned to the assignee of the present application and which is hereby incorporated by reference.

Figure 2:
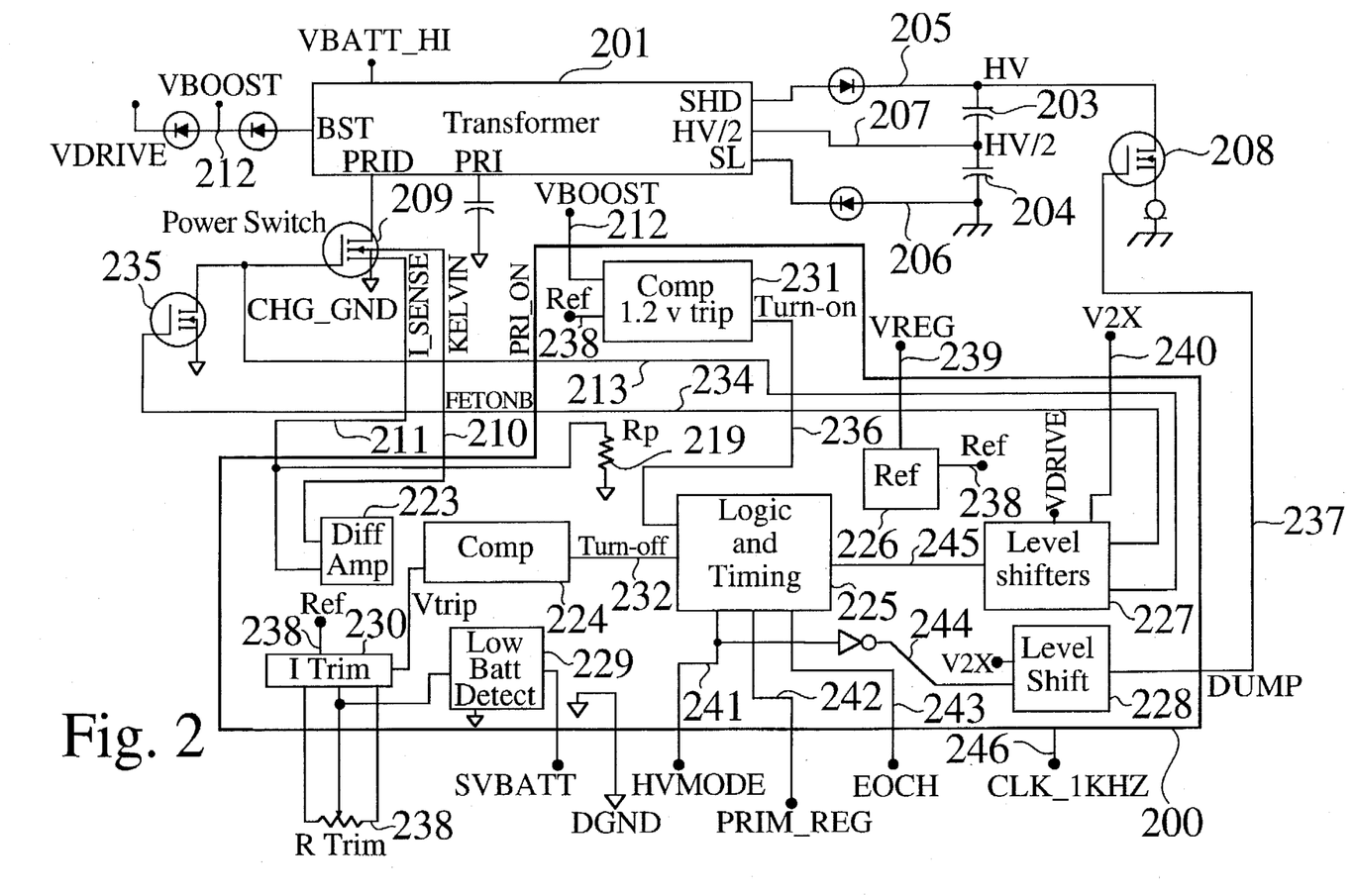
FIG. 2 is a schematic diagram of a high voltage charger in the ICD of FIG. 1.

FIG. 2 is a schematic diagram showing high voltage charger 200 in high voltage charger/output controller circuit 103. Also shown in FIG. 2 is DC-DC converter 201, which provides the charging current to the storage capacitors of high voltage output circuit 104. In the present embodiment, output signals "HV" and "HV/2", represented respectively in FIG. 2 by reference signals 205 and 207, along with ground reference 206, provide currents to charge two series connected capacitors 203 and 204. In the present embodiment, capacitors 203 and 204 are each charged to substantially the same voltage of HV/2. Capacitors 203 and 204 are discharged into an "H" bridge circuit, which allows a biphasic voltage waveform to be provided to defibrillate the patient's heart. When not in "high voltage mode" (see below), transistor 208 discharges capacitors 203 and 204 in response to control signal 237 ("DUMP"), which is obtained by level-shifting an inverted version of control signal HV_MODE at terminal 244. As shown in FIG. 2, a level shifter 228 shifts control signal 208 to the V2X power supply voltage (terminal 240), which is typically six volts.

In the present embodiment, high voltage charger 200 operates in two distinct modes: a 1 KHz mode, which uses a constant 1 KHz switching rate, and a variable rate mode, designed to supply a substantially constant average charging current. Under the 1 KHz mode, based on the clock signal at terminal 246, a relatively low current is drawn from the power source, so that a relatively low charging rate results. The variable rate mode, called "rapid charging", has a variable switching frequency (5–60 KHz) and a relatively constant input current from the power supply, resulting in a maximum output charging rate. To charge capacitors 203 and 204 for a defibrillating discharge, a three-phase charging sequence is provided, consisting of: (i) an initial phase of charging at the 1 KHz mode (the "warm up" period), (ii) a rapid charging phase, and (iii) a final phase of charging at the 1 KHz mode (the "warm down" period). The power supply circuit described in the Copending Application switches its power source from battery 107 to signal VBOOST at the start of the warm up period, and switches back to battery 107 at the end of the warm down period. The initial period of 1 KHz switching allows power supply 102 to switch its regulated supply source to signal VBOOST from system battery 107, whose voltage declines during charging. The ending period of 1 KHz switching allows the battery voltage to recover before being switched back to system battery 107 by power supply circuit 102. The operation of charger 200 is described in a copending patent application ("Copending Application"), filed on the same day as the present application, Ser. No. 08/660,259 entitled "High Voltage Charger" by S. Archer et al, assigned to the assignee of the present application. The disclosure of the Copending Application is hereby incorporated by reference in its entirety.

Figure 3:
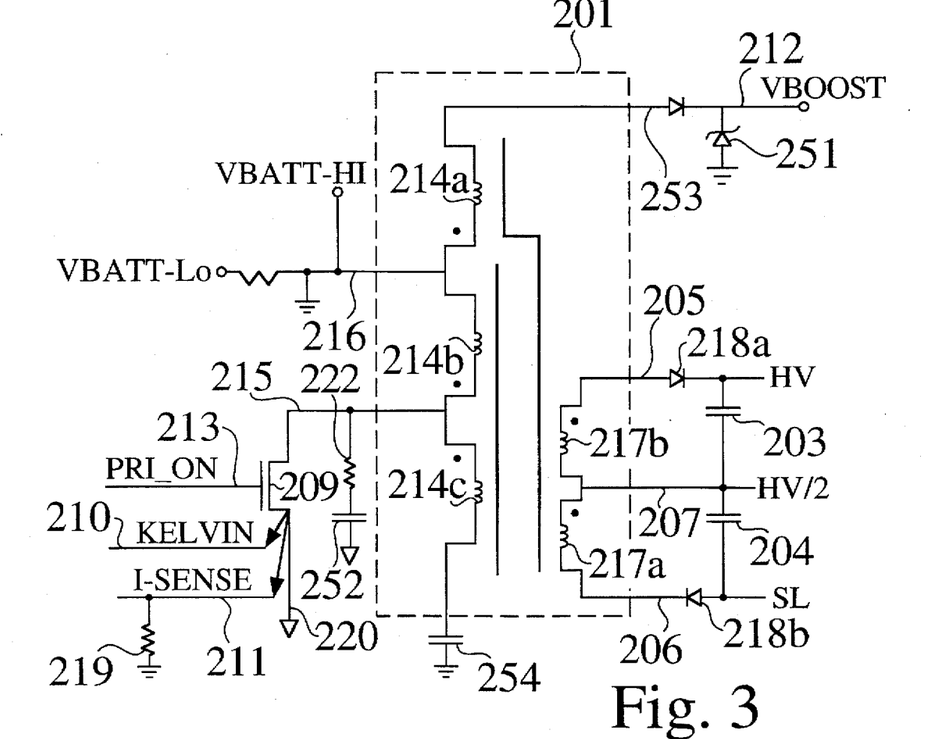
FIG. 3 shows a circuit suitable for implementing DC-DC converter in the ICD of FIG. 1.

FIG. 3 shows a circuit suitable for implementing DC-DC converter 201. As shown in FIG. 3, DC-DC converter 201 includes secondary windings 217a and 217b, which are inductively coupled to primary winding 214c. Windings 214a ("boost winding") and 214b are also inductively coupled to primary winding 214c. DC-DC converter 201 is a step-up converter. Capacitor 254 is provided in DC-DC converter 201 to ensure ripple-free operation. A switch 209 periodically closes to induce a charging current in secondary windings 217a and 217b to charge capacitors 203 and 204 through rectifying diodes 218a and 218b. In this embodiment, switch 209 can be provided by a HEXSENSE current sensing device available from International Rectifier Corporation. HEXSENSE current sensing device 209 is a power metal-oxide-semiconductor (MOS) field effect transistor (FET) with a current sensing capability. In HEXSENSE current sensing device 209, two output source terminals, respectively called the "Kelvin source pin" (pin 210) and the "I_sense source pin" (pin 211) are provided.

I_sense source pin 211 provides a small current (relative to the current in power source terminal 220) which, when measured with respect to the voltage of Kelvin source pin 210, is proportional to the drain current in the HEXSENSE current sensing device 209. Kelvin source pin 210 provides the source voltage of HEXSENSE current sensing device 209. In FIG. 3, resistor 219 couples the current in I_sense source pin 211 to ground. The voltage drop across resistor 219 is thus a quantity proportional to the current in HEXSENSE current sensing device 209. Resistor 222 and capacitor 252 form a series connected RC circuit, which couples the drain terminal of switch 209 to the ground reference voltage in order to reduce switching noise.

HEXSENSE current sensing device 209 is driven at terminal 213 by a signal PRI_ON. Signal PRI_ON is generated by high voltage charger 200 in the manner described in further detail below. When signal PRI_ON switches on HEXSENSE current sensing device 209, current is shunted from winding 214c to HEXSENSE current sensing device 209 rapidly, so that the inductance in DC-DC converter 201 drives signal "VBOOST" at terminal 212 to a high voltage rapidly. In this embodiment, signal VBOOST stays at voltage $V_{hi}$ (10–16 volts) when HEXSENSE current sensing device 209 is on.

When signal PRI_ON switches off HEXSENSE current sensing device 209, triggered by detection of a predetermined current level in I_sense source pin 211, inductance in DC-DC converter 201 drives the signal at terminal 253 negative. With diode 251 preventing signal VBOOST from going below the ground reference voltage, signal VBOOST is consequently driven to the ground reference voltage. Thereafter, while HEXSENSE current sensing device 209 remains off, the magnetic field in the core of DC-DC converter 201 collapses, allowing signal VBOOST to rise from the ground reference voltage to the battery voltage. In rapid charging phase, this rise in voltage in signal VBOOST is used to trigger signal PRI_ON to switch on HEXSENSE current sensing device 209. The triggering of signal PRI_ON at terminal 213 is provided by a logic and timing circuit within high voltage charger 200 described below.

Figure 4:
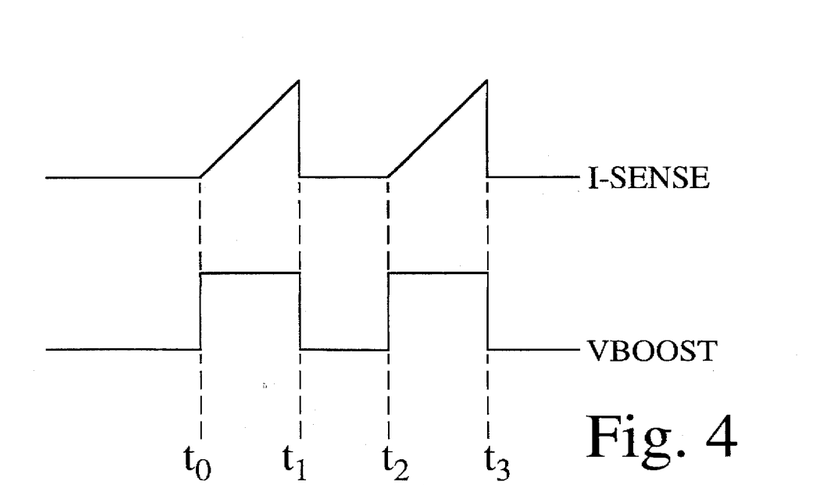
FIG. 4 shows the timing relationship between signal VBOOST and signal I_sense in the high voltage charger during a rapid charging phase.

The timing relationship between signal VBOOST and signal I_sense at terminals 212 and 211, respectively, during the rapid charging phase is illustrated in FIG. 4. Referring to FIG. 2, the differential voltage between Kelvin source pin 210 and I_sense source pin 211, which is proportional to the current in HEXSENSE current sensing device 209, is amplified by a differential amplifier 223 and compared in comparator 224 to a preset threshold voltage $V_{trip}$. When the amplified differential voltage exceeds $V_{trip}$, i.e. the current in HEXSENSE current sensing device 209 exceeds a predetermined threshold, a control signal "turn-off" at terminal 232 is asserted by comparator 224. In the embodiment shown in FIG. 2, $V_{trip}$ is generated by trimming resistor 248 with trim circuit 230 from an internally generated voltage REF at terminal 238. Trimming resistor 248 is also used to provide a low battery condition detection circuit 229 a voltage generated from signal REF. Alternatively, $V_{trip}$ can also be generated by a digital-to-analog converter, using a value specified by controller 101. During rapid charging, logic and timing circuit 225 passes the asserted signal at terminal 245 to level shifter 227 to generate complementary control signals at terminals 213 and 234. The control signal at terminal 213 is signal PRI_ON. In this instance, signal PRI_ON is deasserted to switch off HEXSENSE current sensing device 209. The complementary signal at terminal 234 turns on transistor 235, so as to quickly pull the gate voltage in HEXSENSE current sensing device 209 to the ground reference voltage. FIG. 4 shows the voltage on I_sense source pin 210 abruptly jumps to ground level at each of times $t_1$, and $t_3$, causing corresponding jumps to ground voltage level by signal VBOOST at terminal 212. However, as mentioned above, during the time period between $t_1$, and $t_2$, when HEXSENSE current sensing device 209 remains off, the voltage of signal VBOOST rises at a time determined by levels of charge stored in capacitors 203 and 204. Thus, the frequency of operation in rapid charging phase is the reciprocal of the sum of the on-time ($t_1$–$t_0$) and the off-time ($t_2$–$t_1$) of HEXSENSE current sensing device 209.

Referring back to FIG. 2, signal VBOOST at terminal 212 is compared in comparator 231 with a reference voltage REF at terminal 238, which is derived by reference circuit 226 from signal $V_{REG}$ at terminal 239. Signal $V_{REG}$ is generated by the power supply circuit described in the Copending Application. In this embodiment, when signal VBOOST at terminal 212 exceeds 1.2 volts, a control signal "turn_on" at terminal 236 is asserted, and logic and timing circuit 225 deasserts a control signal at terminal 245. The control signal at terminal 245 causes level shifter 227 to assert control signal PRI_ON at terminal 213 and to deassert the complementary signal "FETONB" at terminal 234. At this time, i.e. either time $t_0$ or time $t_2$ of FIG. 4, current begins to flow in HEXSENSE current sensing device 209, and signal VBOOST at terminal 212 increases rapidly to its maximum value (~15 volts in this embodiment). The present embodiment is designed such that the average current over time in HEXSENSE current sensing device 209 is 2.3 amps, which is believed to be an optimum current for maximizing battery life and for minimizing charge time. Controller 101 (FIG. 1) discharges storage capacitors 203 and 204 by deasserting control signal HV_MODE at terminal 241. Control signal HV_MODE, in turn, asserts control signal "DUMP" at terminal 237, which switches on transistor 208. Transistor 208 couples capacitor 203 to the ground reference voltage.

Figure 5:
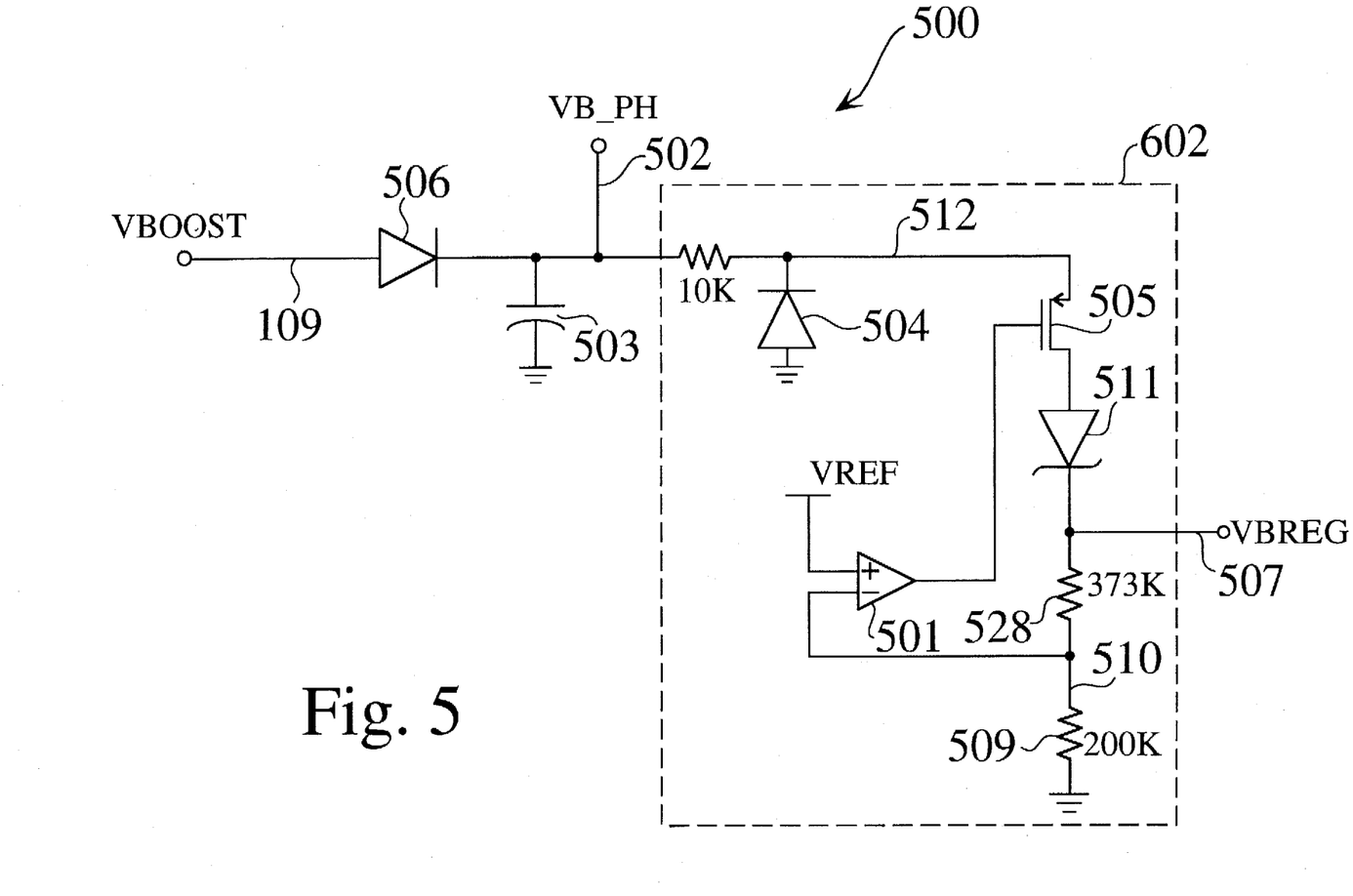
FIG. 5 shows a circuit for generating signal VBREG from signal VBOOST, including a functional unit of a power supply circuit.
Figure 6:
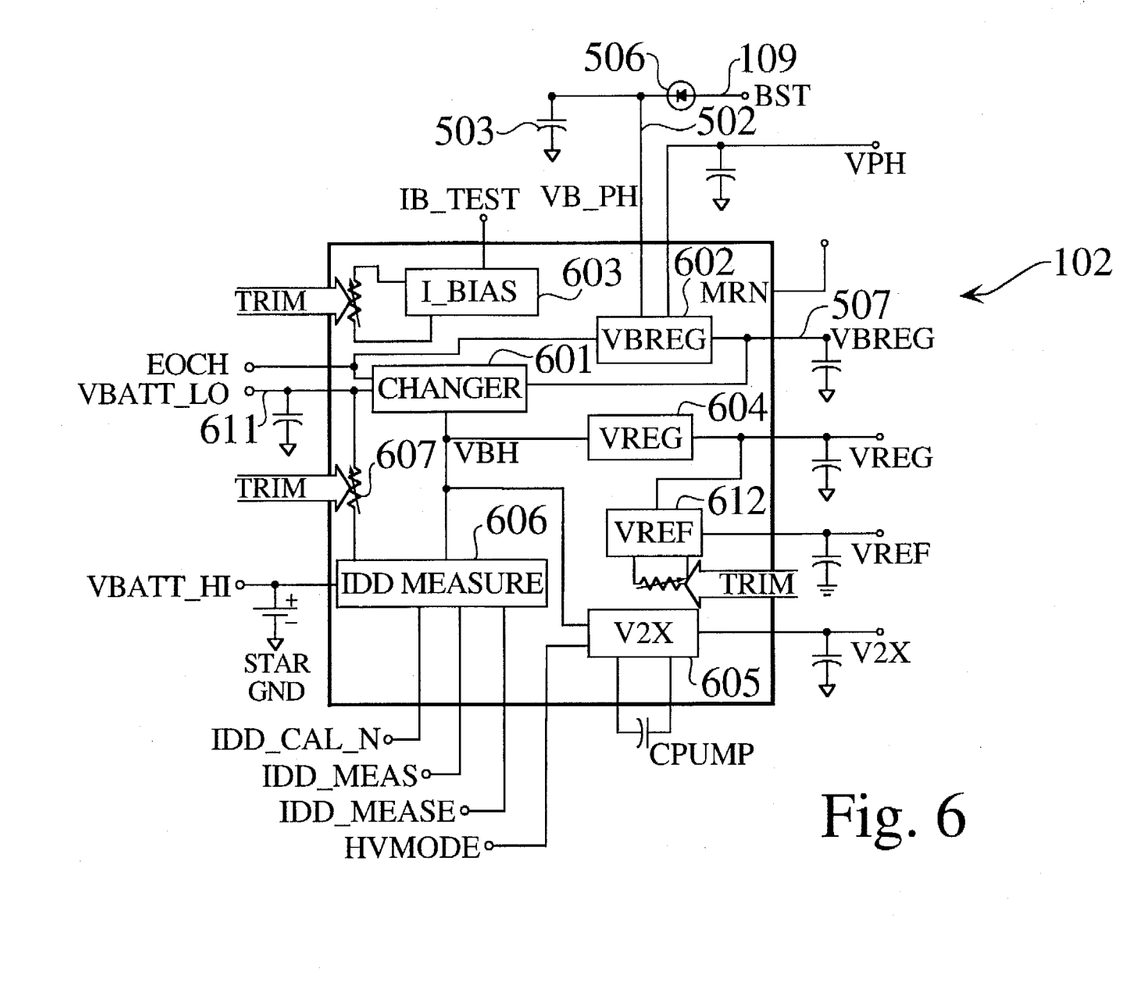
FIG. 6 is a schematic diagram of the power supply circuit.

During the time period when high voltage charger 200 is charging, signal VBREG is used to provide the output voltages of power supply circuit 102, so as to avoid the supply voltage problems associated with the output voltage of battery 107 (i.e. signal VBATT_LO) dipping below an acceptable voltage level. This substitution of power source for power supply circuit 102 is described in conjunction with FIGS. 5 and 6. FIG. 6 is a schematic diagram of power supply circuit 102. FIG. 5 shows circuit 500 for generating signal VBREG from signal VBOOST, including functional unit 602 of power supply circuit 102.

As shown in FIG. 5, signal VBOOST on terminal 109 is rectified by diode 506 to charge a capacitor 503. The voltage on capacitor 503 is an input signal VB_PH on terminal 502 to circuit 602 of power supply circuit 102 (FIG. 6). Diode 504 ensures that the voltage at terminal 512 is above ground reference voltage. Circuit 602 provides an output signal VBREG at terminal 507 to be around 3.3 volts by reference to a reference voltage VREF (~1.1 volts), which is generated in circuit 612 (FIG. 6) by amplifying a bandgap reference voltage. Reference voltage VREF can be very accurately achieved by trimming a resistor. In FIG. 5, a differential amplifier 501 controls the current in P-MOS transistor 505, such that electrical node 510 is at substantially the same voltage as reference voltage VREF. Zener diode 511 is provided to prevent voltage VBREG at terminal 507 from rising above signal VB_PH at terminal 502. Consequently, because signal VBREG is the total voltage drop across resistors 508 and 509, having resistances 373 k-ohms and 200 k-ohms respectively, signal VBREG at terminal 507 is maintained at approximately three times the voltage of signal VREF.

Referring to FIG. 6, voltage VBREG is provided to changer 601 which switches the power supply signal VBH between signals VBATT_LO and VBREG. Signal VBATT_LO (terminal 611) is the voltage at the output terminal (signal "VBATT_HI") of battery 107, minus a voltage drop across a 50 ohms resistor (resistor 607). The switching between signal VBATT_LO and signal VBREG is controlled by control signal EOCH ("end of charging"). EOCH is deasserted throughout the high voltage charging operation. During rapid charging state, a high current is drawn from signal V2X, which is an output voltage of voltage doubler circuit 605.

Power supply circuit 102 generates signal VREG in circuit 604 by amplifying reference signal VREF by a factor of two. A bias circuit 603 is provided to generate bias reference voltages used throughout power supply circuit 102.

Figure 7:
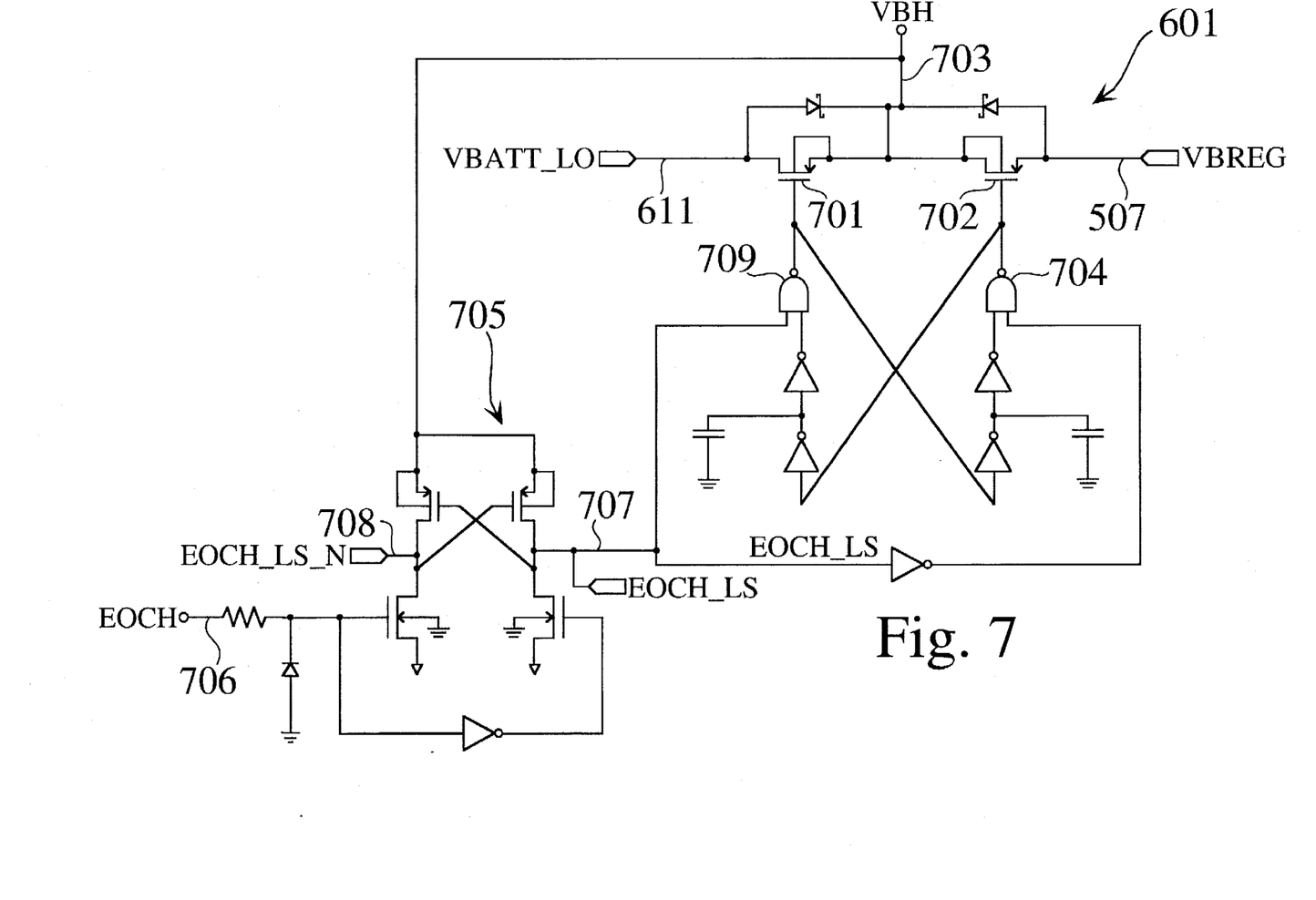
FIG. 7 is a schematic diagram of a changer.

FIG. 7 is a schematic diagram of changer 601. As shown in FIG. 7, signal VBATT_LO, at terminal 611, and signal VBREG, at terminal 507, can be selectively coupled by transistors 701 and 702 to provide output signal VBH at terminal 703. Signal VBH is used to derive all other output power supply signals of power supply circuit 102. Transistors 701 and 702 are controlled by a cross-coupled NAND circuit that includes NAND gates 709 and 704. At any given time, only one of transistors 701 and 702 is conducting. Shown in FIG. 7 also is an amplification circuit 705 which generates from input control signal EOCH (terminal 706) two complementary control signals EOCH_LS and EOCH_LS_N, at terminals 707 and 708, respectively, which are distributed throughout power supply circuit 102 where the control signal EOCH, or its complement, is used. In FIG. 7, control signal EOCH_LS, when asserted, causes transistor 701 to couple signal VBATT_LO to signal VBH. When control signal EOCH_LS is deasserted, signal VBREG is coupled to signal VBH.

Figure 8:
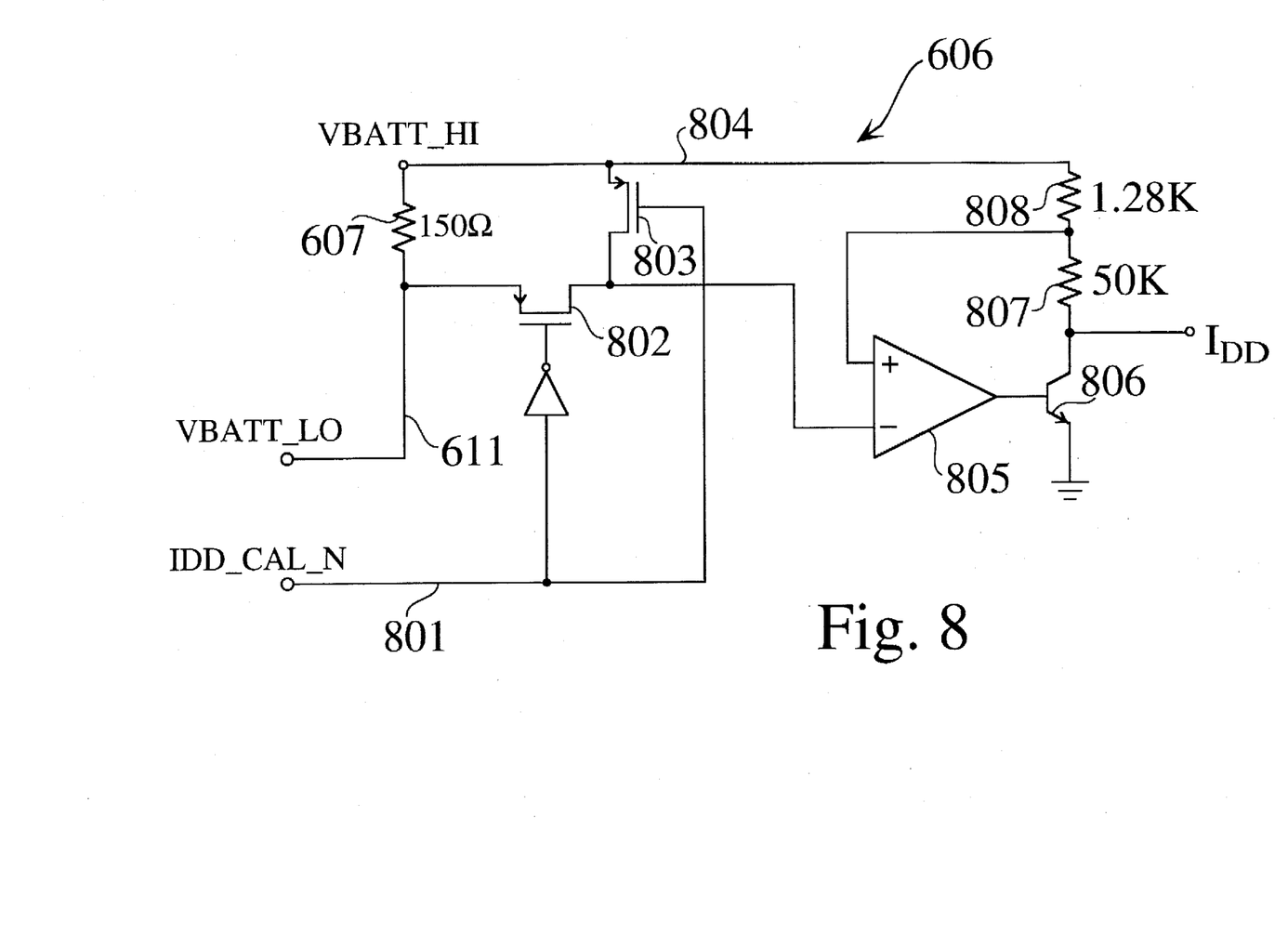
FIG. 8 is a schematic diagram of an IDD measurement circuit.

Since power in ICD 100 is drawn through signal VBATT_LO, the voltage across resistor 607 provides a measure of the total current (hence total power) drawn by ICD 100. System current measurement circuit 606 measures the current across resistor 607. FIG. 8 is a schematic diagram of system current measurement circuit 606. As shown in FIG. 8, system current measurement circuit 606 operates under one of two modes: the measurement mode and the calibration mode, selected by control signal IDD_CAL_N. Measurement mode is entered when signal IDD_CAL_N at terminal 801 is asserted. In measurement mode, transistor 802 couples terminal 611 (i.e. signal VBATT_LO) to an input terminal of differential amplifier 805. When IDD_CAL_N is deasserted, transistor 803 couples terminal 804 to the same input terminal of differential amplifier 805. Differential amplifier 805 controls the current in transistor 806. Hence, under measurement mode, the voltage drop across resistors 807 and 808 is proportional to the voltage drop across resistor 607, i.e. the current drawn by ICD 100 from battery 107. Under calibration mode, the voltage drop across resistors 807 and 808 is proportional to the voltage drop across resistor 808, i.e. the current drawn by system current measurement circuit 606.

The above detailed description is provided to illustrate the specific embodiments of the present invention and is not intended to be limiting. Numerous variations and modifications within the scope of the present invention are possible. The present invention are defined by the appended claims.

We claim:

1. A power supply circuit receiving power from a battery, comprising:

a transformer, coupled to said battery, said transformer including a primary winding and a boost winding providing an output voltage;

a changer providing a voltage source, said changer deriving said voltage source alternatively between said battery and said output voltage of said boost winding; and a plurality of regulated power supply circuits each providing an output voltage based on said voltage source.

2. A power supply circuit as in claim 1, wherein one of said plurality of regulated power supply circuits includes a circuit for generating a voltage reference signal using a semiconductor bandgap voltage.

3. A power supply circuit as in claim 1, wherein said boost winding and said primary winding form a step-up converter.

4. A power supply circuit as in claim 1, wherein said power supply circuit supplies power to a high voltage charger for an output circuit including storage capacitors, said power supply circuit deriving said output voltage source from said output voltage of said boost winding during time periods when said high voltage charger charges said storage capacitors.

5. In a power supply circuit, a method for preventing regulated output signals from falling below operational values as a result of a high current being drawn from said power supply circuit, said method comprising the steps of:

providing a voltage source through a changer circuit, said changer circuit deriving said voltage source from an output voltage of a boost winding of a step-up converter; and from said voltage source, generating a plurality of regulated power supply output signals.

6. A method as in claim 5, wherein one of said plurality of regulated power supply output signals is generated from a voltage reference signal using a semiconductor bandgap voltage.

7. A method as in claim 5, wherein said power supply circuit supplies power to a high voltage charger for an output circuit including storage capacitors, said power supply circuit deriving said output voltage source from said output voltage of said step-up converter during time periods when said high voltage charger charges said storage capacitors.

* * * * *